United States Patent [19]

Bozzuto

[11] Patent Number: 4,487,683
[45] Date of Patent: Dec. 11, 1984

[54] ACETYLENE FROM COAL AND AN ELECTRIC ARC

[75] Inventor: Carl R. Bozzuto, Enfield, Conn.

[73] Assignee: Combustion Engineering, Inc., Windsor, Conn.

[21] Appl. No.: 401,806

[22] Filed: Jul. 26, 1982

[51] Int. Cl.³ .......................... C10G 1/00; C10B 57/16
[52] U.S. Cl. ...................................... 208/8 R; 585/539; 585/538
[58] Field of Search ................ 208/8 R; 585/539, 538

[56] References Cited

U.S. PATENT DOCUMENTS

| | | | |
|---|---|---|---|
| 3,384,467 | 5/1968 | Ammann et al. | 208/8 R |
| 4,010,089 | 3/1977 | Stowell et al. | 208/8 R |
| 4,010,090 | 3/1977 | Fey et al. | 208/8 R |
| 4,105,888 | 8/1978 | Fey | 585/539 |
| 4,358,629 | 11/1982 | Kim | 208/8 R |
| 4,378,232 | 3/1983 | Peuckert et al. | 585/539 |
| 4,412,908 | 11/1983 | Yamashita et al. | 208/107 |

OTHER PUBLICATIONS

Chen, *Introduction to Plasma Physics*, pp. 1–16, 321, Plenum Press, New York 1974.
Hellund, *The Plasma State*, pp. 33–101, Reinhold Publishing Corp., New York, 1961.
Krukonis et al., "Deuterium and Carbon-13 Tagging Studies of the Plasma Pyrolysis of Coal", *Coal Gasification*, Advances in Chem. Series, No. 131, ACS 1974.

Primary Examiner—Delbert E. Gantz
Assistant Examiner—Lance Johnson
Attorney, Agent, or Firm—Troxell K. Snyder

[57] ABSTRACT

A process for producing hydrocarbons suitable for use as a chemical feedstock uses coal (10) and methane-rich gas (56) as raw materials. The coal and gas are heated over 6000° F. (3316° C.) in an electric-arc (14) forming an atomic plasma (16). The plasma is cooled and held (18) between 5000° and 6000° F. (2760° and 3316° C.) to allow formation of the desired hydrocarbons. The product stream (22) is then quenched (24) and the hydrocarbons separated (40, 42).

9 Claims, 1 Drawing Figure

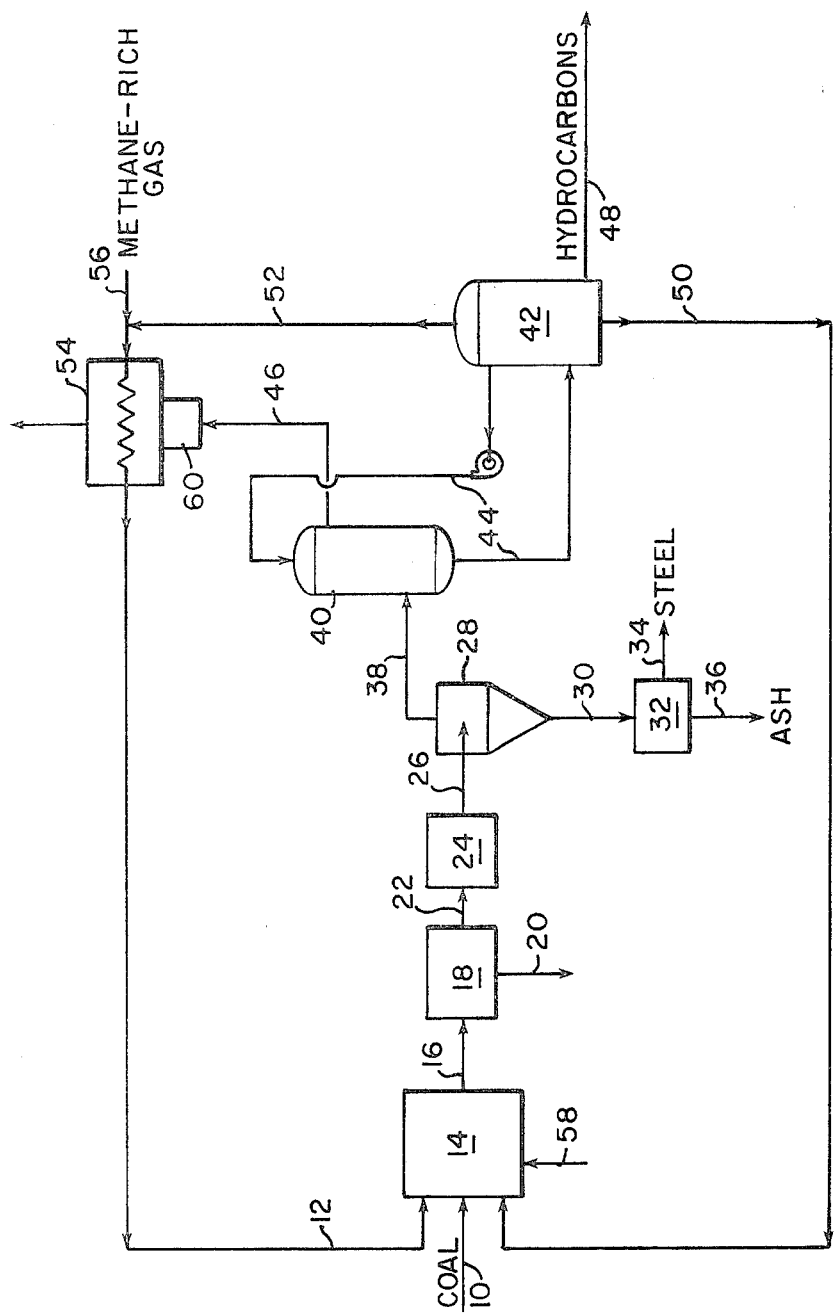

ACETYLENE FROM COAL AND AN ELECTRIC ARC

BACKGROUND OF THE INVENTION

1. Field of the Invention

This invention pertains to a process for producing hydrocarbons and more particularly to a process for producing hydrocarbons from coal.

2. Prior Art

As a result of the shortage of petroleum products in the world market in recent history it has become more desirable to seek hydrocarbon feedstocks for chemical processes from other sources. One possible source of hydrocarbon feedstock is by the conversion of coal.

A desirable hydrocarbon feedstock is acetylene, $C_2H_2$, which is more reactive than ethylene, $C_2H_4$, the present primary feedstock for many processes. Acetylene would thus replace ethylene if they were equal in price. Since ethylene is presently made from petroleum, there is great interest in the chemical industry in finding a new source of equivalent chemical feedstock.

Present methods of converting coal to alternative fuels include gasification and devolatilization. Gasification produces primarily carbon monoxide, CO, and hydrogen gas $H_2$. Gasification processes attempt to minimize the formation of hydrocarbons in the gasification process to avoid fouling the gas flow passages within the equipment. On the other hand, devolatilization of coal not only requires disposal of the large amount of carbon left over after the devolatilization process, but also produces higher hydrocarbons which may be carcinogenic or otherwise hazardous.

All of the processes in the prior art for converting coal to an alternative form have required the addition of heat energy to the coal in order to effect the conversion reaction. One method of adding heat has been through the use of an electric-arc. U.S. Pat. No. 3,384,467 (prior art statement) by Ammann et. al discloses the use of an electric-arc to devolatilize the coal, producing primarily hydrogen gas and unreacted carbon. The disposal of this unreacted carbon and the lack of suitable hydrocarbons present in the reaction product makes this process unsuitable for converting coal to chemical feedstock.

Another method for producing acetylene requires blowing coal with a hydrogen gas carrier through an electric-arc at some 4,900 F. (2704 C.). The reaction products of this reaction are claimed to be 30% acetylene, 20% low to mid BTU gases, such as CO, $CH_4$, etc. and 50% char, unreacted coal and carbon black. This method, while resulting in a significant fraction of the input constituents being converted to a desirable chemical feedstock, requires a supply of hydrogen gas. The production of hydrogen gas is a costly and complicated process and would be undesirable for use in a large scale facility.

In summary the processes of the prior art either do not convert a significant portion of the coal to the desired hydrocarbon feedstock, or require the addition of hydrogen gas to the coal prior to reaction. The resulting inefficiency and complexity of the prior art processes have made industry reluctant to adopt coal conversion as a means for producing hydrocarbon feedstock.

SUMMARY OF THE INVENTION

The present invention provides a process for producing hydrocarbon feedstock such as acetylene, $C_2H_2$, from coal and methane-rich gas, such as natural gas. The process subjects the coal and gas to a high energy electric-arc wherein these reactants are completely dissociated into a plasma of atoms. The atomic plasma leaving the arc is then cooled and held in a suitable temperature range in which the formation of hydrocarbon feedstock is favored by thermodynamic equilibrium.

The products are then quickly quenched to maintain this equilibrium composition and separated to form process streams of solids, hydrocarbons and a combustible fuel gas.

The fuel gas may be used to generate energy for other process uses or to preheat the methane-rich feed to the electric-arc. The separated solids may be further divided into a stream of inert waste compounds for disposal and a stream of steel formed from the iron present in coal ash.

By the addition of a sulfur absorbing compound to the electric-arc, the sulfur present within the coal is absorbed and rejected from the process as a solid sulfide.

BRIEF DESCRIPTION OF THE DRAWING

The FIGURE shows a flow schematic for a process according to this invention.

DESCRIPTION OF THE PREFERRED EMBODIMENT

Referring now to the FIGURE, a stream of coal 10 and a stream 12 of methane-rich gas, such as natural gas, are shown entering the electric-arc furnace 14. The coal is preferably pulverized to facilitate vaporization within the arc furnace and well-mixed with the methane. Peak temperature within the electric-arc is in excess of 6,000 F. (3316 C.) and preferably in the range of 8,000 to 10,000 F. (4427 to 5538 C.). At temperatures in this range the chemical compounds present in the coal and methane are dissociated into their atomic constituents and form an atomic plasma at the exit 16 of the arc furnace.

The atomic plasma is then cooled in the cooler 18 to an intermediate temperature favorable for the formation of desirable hydrocarbons. Thermodynamic equilibrium calculations show this temperature to be in the range of 5,000 to 6,000 F. (2760 to 3316 C.). This temperature range has been selected based on calculations showing the continued dissociation of the atomic plasma at temperatures in excess of 6,000 F. (3316 C.) and the unfavorable equilibrium conditions for the formation of desirable hydrocarbons below 5,000 F. (2760 C.). The length of time at which the gas must be held between 5,000 and 6,000 F. (2760 and 3316 C.) is less than approximately 60 milliseconds which is sufficient to allow a significant amount of the desired hydrocarbons to form.

Exiting from the cooler 18 is a waste stream 20 which contains liquid slag comprised of silicon dioxide, aluminum oxide and other inert ash compounds originally present in the coal feed. The product stream 22 exiting the cooler contains primarily hydrocarbons such as acetylene, $C_2H_2$, benzene, $C_6H_6$, and medium-BTU fuel gas composed mainly of carbon monoxide, CO, and hydrogen $H_2$.

The product stream is then quickly reduced in temperature below approximately 2000 F. (1093 C.) in less than 30 milliseconds by the quench step 24. This step effectively stops the chemical interaction among the components of the product gas stream 26 due to the relatively slow chemical reaction rates present at these temperatures. Quenching may be accomplished by any number of methods old in the art such as spraying the mixture with water or adding a large amount of cool, inert gas.

The composition of the quenched stream 26 is thus substantially equivalent to that of the product stream 22. Without the rapid quenching step, the components of the product stream 22, especially the hydrocarbons, would continue to interact chemically and move toward the equilibrium composition for the particular temperature level, thus resulting in little or no hydrocarbons present in the final gas stream.

In the preferred embodiment, the quenched gas stream 26 next enters a separator 28 for removing solid particulate matter present at this stage of the process. This particulate matter removed 30 consists primarily of solid inert ash compounds originally present within the coal feed. For some coals at least a portion of this matter is ferrous and, as a result of the reducing atmosphere present within the upstream chemical process, is present in the waste stream 30 as steel which may be magnetically separated 32. The steel thus separated 34 is retained for sale or use while the remainder of the ash 36 is sent to disposal.

The product stream 38 exiting the separator 28 is relatively solids-free and consists primarily of hydrocarbons, carbon monoxide, and hydrogen. This stream enters the scrubber 40 which removes the hydrocarbons from the gases by means of a solvent circulated between the scrubber 40 and the oil separator 42. The circulation streams are noted in the FIGURE by the process flow stream lines 44. The stream exiting the scrubber 46 is a clean, medium BTU fuel gas consisting primarily of carbon monoxide and hydrogen.

The oil separator 42 removes the desired hydrocarbons 48 from the circulating solvent. Typical solvent compositions may be benzene, cyclohexanone, or any other material capable of dissolving or absorbing the desired hydrocarbons.

There may also be present within the scrubber solvent other materials removed from the product stream such as solids 50 or gases 52 which are separated from the solvent in the separation step 42. Both of these streams are recycled to the electric-arc furnace 14 for further reaction as shown in the FIGURE.

The medium BTU fuel gas stream 46 is a clean fuel which may be used or sold. In the preferred embodiment, this stream is shown flowing into a burner 60 and heat exchanger 54 which preheat the methane-rich feed stream 56 flowing to the electric-arc furnace 14.

Coal also contains sulfur in varying amounts. This sulfur may be absorbed within the process by the addition of calcium carbonate, $CaCO_3$, or other sulfur absorbent compound 58 to the feed to the electric-arc furnace 14. Where a calcium bearing compound such as $CaCO_3$ is added, the sulfur reacts to form calcium sulfide, CaS, which will condense out downstream as a liquid in the slag stream 20 or as solid particulate in the solid particulate stream 30. Another potential material for the absorption of sulfur is potassium which forms potassium sulfide, $K_2S$.

The process according to the present invention is thus seen to efficiently and completely react coal and natural gas to form hydrocarbon feedstock for use in chemical processes. The use of a methane-rich gas instead of hydrogen to supplement the hydrogen content of the coal is advantageous in that methane is readily available in natural gas whereas the hydrogen required in the prior art must be manufactured. Other advantages of the present invention include the production of medium BTU fuel gas for possible use either within the process or for other purposes, and the removal of the ferrous material originally present in the coal as steel.

I claim:
1. A process for producing acetylene from coal and methane-rich gas comprising the steps of:
    (a) heating said coal and said methane-rich gas to a peak temperature over 6000° F. in an electric-arc to form a plasma;
    (b) cooling the plasma of step (a) to less than 6000 F.;
    (c) maintaining the temperature of the cooled plasma at a temperature within the range of 5000 to 6000 F. for approximately 60 milliseconds to form a substantially equilibrated mixture of chemical compounds including said acetylene; and
    (d) quickly quenching the compounds following step (c) to a substantially lower temperature in less than 30 milliseconds whereby the chemical activity between the formed compounds is substantially stopped and the chemical composition of the quenched mixture is maintained substantially unchanged.

2. The process of claim 1 wherein the peak temperature in step (a) is in the range of 8,000 to 10,000 F.

3. The process of one of claims 1 or 2 comprising the additional step of:
    (e) separating at least a portion of the acetylene from the compounds produced in step (c), leaving a combustible fuel gas.

4. The process of claim 3 comprising the additional step of:
    (f) mixing at least a portion of the combustible fuel gas obtained in step (e) with a methane-rich gas and feeding the mixture to the electric-arc of step (a).

5. The process of claim 3 comprising the additional step of:
    (g) combusting at least a portion of the fuel gas obtained from step (e) in a heat exchange device for heating the methane-rich gas fed to the electric-arc in step (a).

6. The process of claim 4 comprising the additional step of:
    (g) combusting at least a portion of the fuel gas obtained from step (e) in a heat exchange device for heating the methane-rich gas fed to the electric-arc in step (a).

7. The process of claim 2 comprising the additional steps of:
    (h) separating inert ash compounds from the compound mixture of step (c); and
    (i) separating the ash compounds from step (h) into a ferrous portion and a nonferrous portion, whereby steel may be recovered.

8. The process of one of claims 1 or 2 comprising the additional steps of:
    (j) feeding an additional sulfur absorbent compound to the electric-arc of step (a) for absorbing sulfur present within said coal; and
    (k) separating the absorbed sulfur from said acetylene and the combustible fuel gas.

9. The process of claim 8 wherein the sulfur absorbent compound is a calcium bearing compound.

* * * * *